United States Patent [19]

Walshe

[11] 4,170,717

[45] Oct. 9, 1979

[54] ELECTRONIC STETHOSCOPE

[76] Inventor: James C. Walshe, 9335 Lubec St., Downey, Calif. 90240

[21] Appl. No.: 914,732

[22] Filed: Jun. 12, 1978

Related U.S. Application Data

[63] Continuation of Ser. No. 770,224, Feb. 18, 1977, abandoned.

[51] Int. Cl.$^2$ .............................................. A61B 7/04
[52] U.S. Cl. ................................................ 179/1 ST
[58] Field of Search .................. 179/1 ST; 128/2.05 S

[56] References Cited

U.S. PATENT DOCUMENTS

| | | | |
|---|---|---|---|
| 3,182,129 | 4/1965 | Clark et al. ......................... | 179/1 ST |
| 3,247,324 | 4/1966 | Cefaly et al. ....................... | 179/1 ST |
| 3,539,724 | 11/1970 | Keeseb ............................... | 179/1 ST |

FOREIGN PATENT DOCUMENTS 1343679 of 1963 France .................................. 179/1 ST Primary Examiner—Kathleen H. Claffy
Assistant Examiner—E. S. Kemeny
Attorney, Agent, or Firm—William W. Haefliger

[57] ABSTRACT

A portable, lightweight, self-contained stethoscope includes:
 (a) an enclosure containing a speaker, and having an acoustic wave outlet port connectible to stethoscope flexible tubing,
 (b) a housing,
 (c) a transducer carried by the housing, the transducer including a microphone located to be placed in proximity to a patient's body,
 (d) circuitry in the housing and having an input terminal coupled with the transducer, said circuitry including amplifier means and filter means, and a battery power supply coupled with said circuitry, said circuitry having a first output terminal, and
 (e) flexible connection means coupling said first output terminal with said speaker.

3 Claims, 6 Drawing Figures

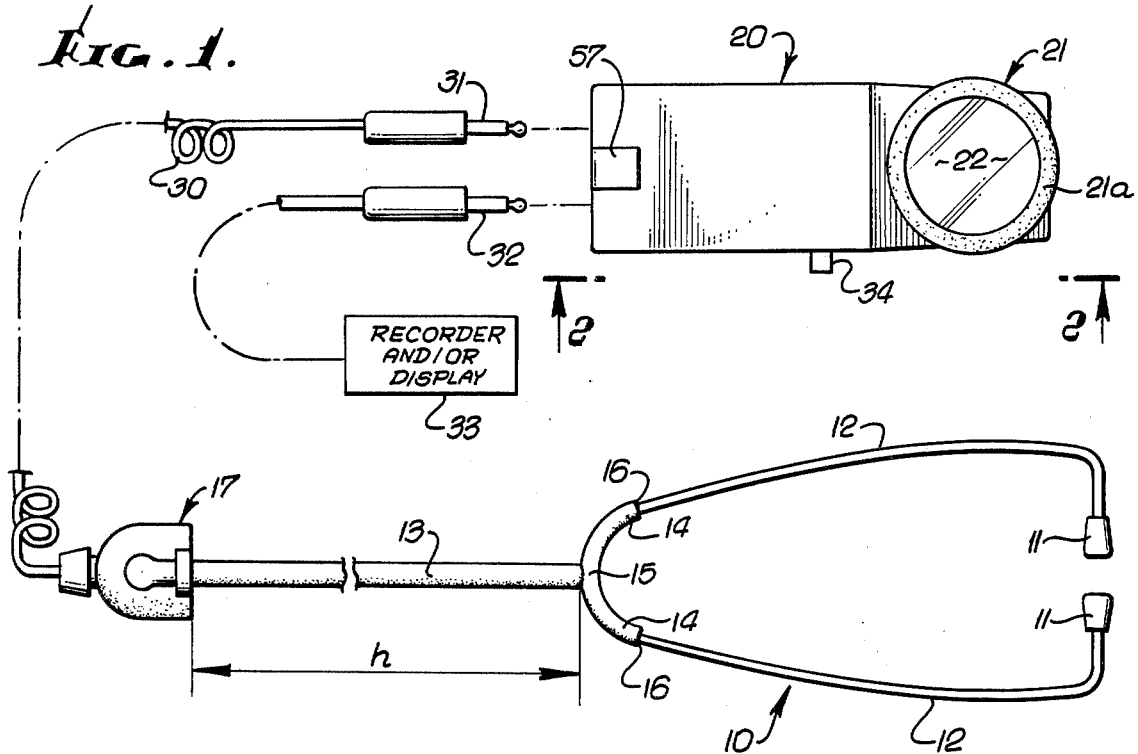
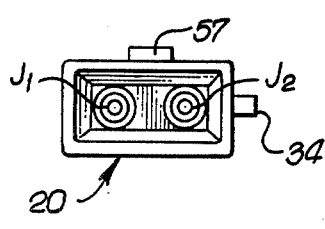
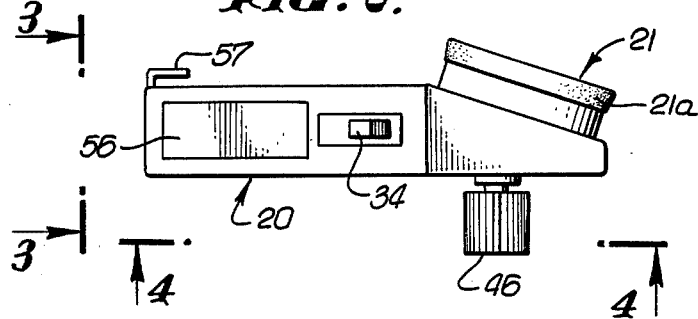
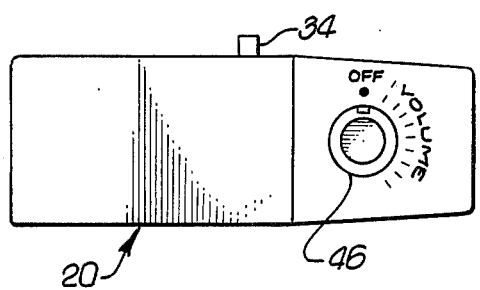

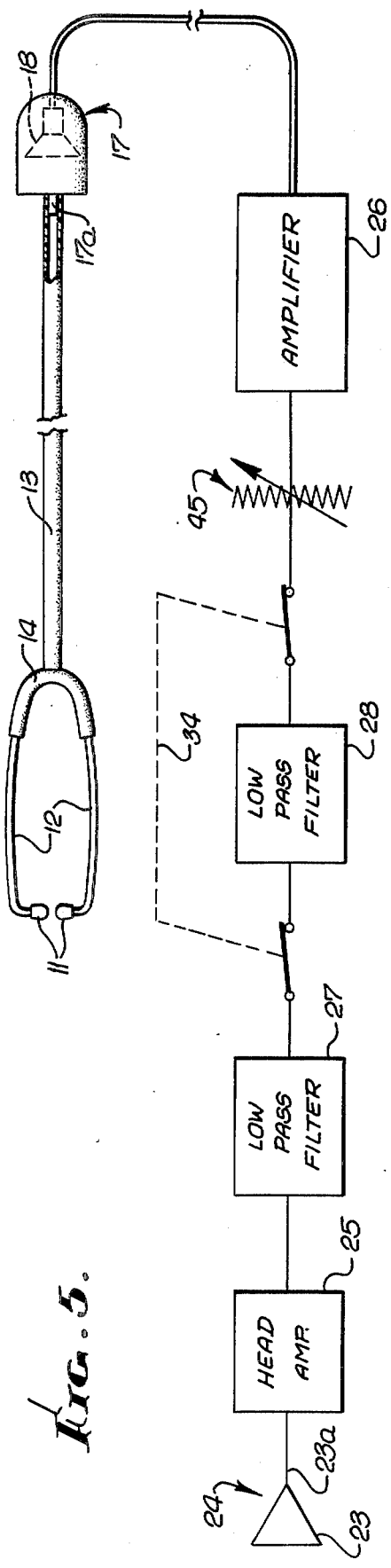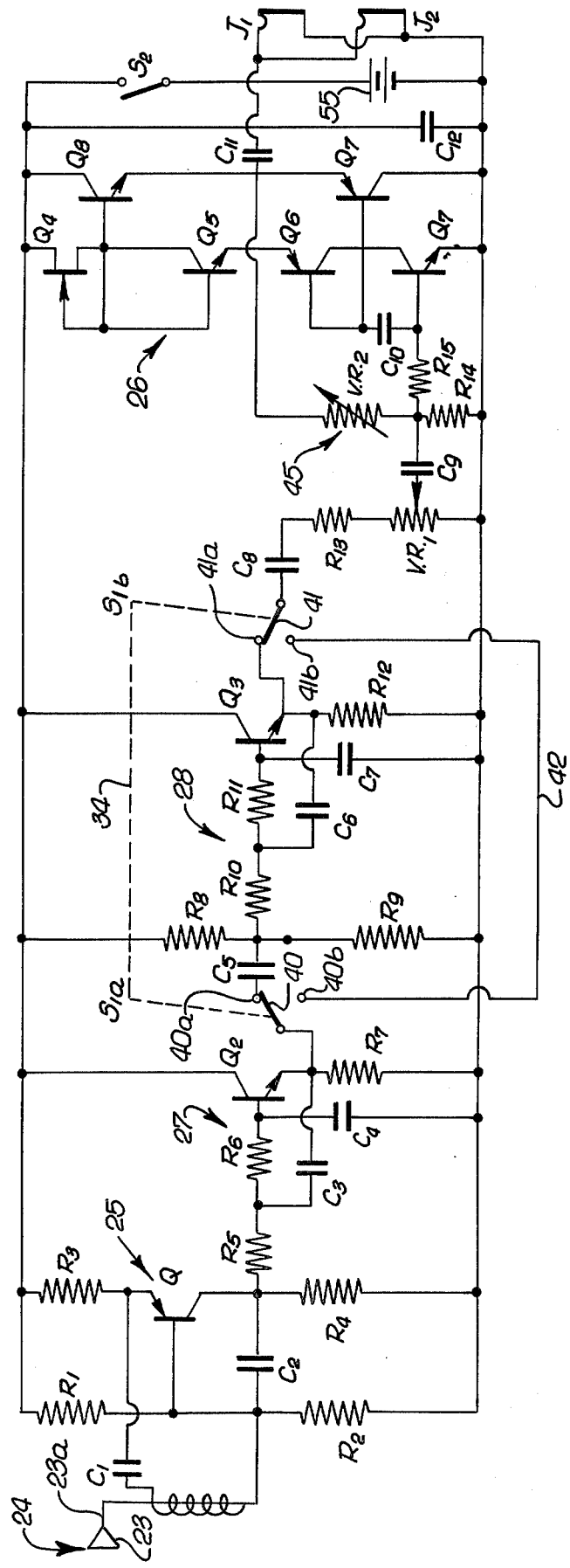

ELECTRONIC STETHOSCOPE

This is a continuation of application Ser. No. 770,224, filed Feb. 18, 1977, now abandoned.

BACKGROUND OF THE INVENTION

This invention relates generally to stethoscopes, and more particularly concerns an electronic stethoscope of wide adaptability and high efficiency.

Prior stethoscopes have suffered certain disadvantages, and have lacked advantages as are found in the present electronic unit. For example, no way was known, to my knowledge, to adapt electronic circuitry to an existing binaural pick-up in the unusually advantageous manner as now provided by the present invention. Also, the use of expensive circuitry is avoided.

SUMMARY OF THE INVENTION

It is a major object of the invention to provide an electronic stethoscope affording numerous advantages, including adaptability to existing binaural pick-ups, high sensitivity including capability to selectively discriminate between body sounds of high and low frequency; light weight construction; selective recording capability; simplicity and other features and advantages as will appear. Fundamentally, the stethoscope comprises:

(a) an enclosure containing a speaker, and having an acoustic wave outlet port connectible to stethoscope flexible tubing,
(b) a housing
(c) a transducer carried by the housing, the transducer including a microphone located to be placed in proximity to a patient's body,
(d) circuitry in the housing and having an input terminal coupled with the transducer, said circuitry including amplifier means and filter means, and a battery power supply coupled with said circuitry, said circuitry having a first output terminal, and
(e) a flexible connection means coupling said first output terminal with said speaker.

As will appear, the body may contain sockets for interchangeable jack plugs leading to the speaker and to a recorder and/or associated display, the filter means may include two low pass filters, one or both of which may be selectively coupled to amplifier means to control the cut-off level of transmitted frequencies (for example, heart sounds may be isolated from other body sounds); and the speaker enclosure may be located between an extensible and flexible cord (connected to the circuit in the housing via a jack) and stethoscope flexible tubing, as will appear. Further, isolation of body sounds can be achieved through selective use of volume control and adjustable filtering. Such sounds include, but are not limited to, those produced by the heart, pulse, blood pressure and those associated with respiratory, peristalsis and fetal functions. Also, a battery to power the circuit may be carried in the housing, and a single control on the housing may control ON-OFF and gain (output volume) of the circuitry. Therefore no separate amplifier box or battery pack is required. Finally, the apparatus is light weight, may be hand-held and is portable.

These and other objects and advantages of the invention, as well as the details of an illustrative embodiment, will be more fully understood from the following description and drawings, in which:

DRAWING DESCRIPTION

FIG. 1 is a plan view showing stethoscope apparatus embodying the invention;

FIG. 2 is a side elevation taken on lines 2—2 of FIG. 1;

FIG. 3 is an end view on lines 3—3 of FIG. 2;

FIG. 4 is bottom plan view taken on lines 4—4 of FIG. 2;

FIG. 5 is a block diagram of circuitry embodied in the apparatus; and

FIG. 6 is a circuit diagram.

DETAILED DESCRIPTION

In the drawings, the stethoscope apparatus is shown to include a binaural acoustic stethoscope 10 having earpieces 11 connected to metallic ducts 12. Acoustic waves are delivered to such ducts via a flexible duct 13 of length "h," and flexible tubular duct branches 14 connected at 15 to duct 13 and at 16 to ducts 12. Length "h" is preferably about 19 inches, for best results.

Coupled to the input end of duct 13 is a lightweight enclosure 17 (which may consist of plastic material). The enclosure contains a small speaker 18, and has an outlet port communicating with the duct 13, whereby acoustic waves generated by the speaker are directly transmitted to the stethoscope duct 13. See FIG. 5 in this regard. The output port may be formed by a small tubular nipple 17a integral with enclosure 17 and telescopically fitting the end of flexible duct 13, whereby existing, non-electronic stethoscope may be readily fitted to the enclosure 17, i.e. coupled to the electronic apparatus of the invention. An output amplifier may also be incorporated in the enclosure, if desired, and connected to the speaker.

Also shown in the drawings is an elongated housing 20 carrying a body piece 21, which includes an annular ring 21a made of soft plastic or elastomeric material to be comfortably (for example with no chill) placed against a patient's body or clothing covering same. A thin diaphragm 22 extends across the opening formed by ring 21a and may be part of, or acoustically coupled to, the pick-up michrophone 23. The microphone and/or diaphragm may be considered as a transducer 24 operable to convert acoustic pulses, i.e. heart beats, to electrical signals at microphone output 23a. The housing 20 is readily hand-manipulated to place the body piece against the patient's body, or clothing covering same, so that the microphone is able to pick-up body sounds.

Extending the description to FIGS. 5 and 6, the housing contains circuitry having an input terminal (i.e. at 23a) coupled to the transducer 24, the circuitry including amplifier means and filter means and at least one output terminal. As seen in FIG. 5, the amplifier means includes an input section 25 and an output section 26, and the filter means includes low pass filters 27 and 28.

First and second output terminals are indicated in FIG. 6 at $J_1$ and $J_2$ which may advantageously be defined by jack connection sockets also seen in FIG. 3. Either of the sockets may be coupled to the speaker 18, as via flexible connection means such as flexible cord 30. The latter has a jack plug 31 at one end, the plug interfitting either socket $J_1$ and $J_2$. An electrical wire within the cord connects the plug to the speaker 18, (or amplifier) within enclosure 17. A second jack plug 32 is sized to fit either socket $J_1$ and $J_2$, and is connected with a recording device, and/or an associated display, indicated at 33.

A manually controllable element, such as slide button 34 on the housing, is connected with the low-pass filter means to adjust same between a first position in which both filters 27 and 28 are connected between the amplifier sections 25 and 26, and a second position in which only filter section 27 is connected between the amplifier sections. Accordingly, the filter means is adjustable to cut-off at one frequency level when both filters are connected in series, and another level when only one filter is operative, whereby the user may more easily discriminate between different body sounds.

Switch means is typically provided, and operated by element 34, to connect one or both the filters in series with the amplifiers. For example, note gang connected switch arms 40 and 41. In up-positions of the arm, they contact terminals 40a and 41a to connect filter section 28 in series with section 27; whereas, in down positions of the arms, they contact terminals 40b and 41b which are joined by a by-pass line 42, disconnecting filter section 28 from section 27.

The circuitry also includes adjustable means to control the amplitude of the signal transmitted to the speaker 18, and a manually controllable part is located on the housing to adjust the adjustable means. The latter may include a potentiometer indicated at 45 in FIGS. 5 and 6 as coupled between filter section 28 and amplifier section 26. A knob 46 on the housing controls the potentiometer.

An on-off switch is indicated at $S_2$, and may also be controlled by knob 46, i.e. to turn ON when the knob is initially rotated from OFF position (thereafter, turning of the knob controls the potentionmeter).

Typical circuit elements are indicated at follows:
Q-1—2SA701F
Q-2—2SC693G
Q-3—2SC693G
Q-4—2SK50
Q-5—2SC693F
Q-6—2SA701F
Q-7—2SC693G
Q-8—2SC693F
Q-9—2SA701F
R-1—15 K ohm
R-2—47 K ohm
R-3—3.9 K ohm
R-4—15 K ohm
R-5—15 K ohm
R-6—15 K ohm
R-7—4.7 K ohm
R-8—8.2 K ohm
R-9—10 K ohm
R-10—15 K ohm
R-11—15 K ohm
R-12—4.7 K ohm
R-13—1 K ohm
R-14—22 K ohm
R-15—10 K ohm
C-1—100 μF
C-2—100 μF
C-3—10 μF
C-4—0.047 μF
C-5—33 μF
C-6—0.1 μF
C-7—47 μF
C-8—33 μF
C-9—15 μF
C-10—1 μF
C-11—100 μF
C-12—100 μF
VR-1—5 K ohm
VR-2—100 K ohm
Frequency Response:
(L)—20–200 Hz
(H)—50–1,500 Hz
Power Consumption—4.7 ma
Battery: 4G13/6 volts
Battery Life: 32 hours+

A battery indicated at 55 may be carried within the housing, and accessible via door 56. A clip 57 on the housing enables carriage of the latter in a pocket, after disconnection of cord 30 at the jack location.

I claim:

1. In a portable, lightweight, self-contained electronic stethoscope, the combination comprising
   (a) a lightweight enclosure containing a speaker,
   (b) a housing separate and remote from said enclosure,
   (c) a transducer carried by the housing, the transducer including a microphone located to be placed in proximity to a patient's body, the microphone having an exposed diaphragm to acoustically couple to the patient's body,
   (d) circuitry in the housing and having an input terminal coupled with the transducer, said circuitry including amplifier means and filter means, and a battery power supply in the housing and coupled with said circuitry, said circuitry having a first output terminal,
   (e) flexible electrical connection means outside the housing and coupling said first output terminal with said speaker, said connection means including a flexible and extensible cord,
   (f) said circuitry including adjustable means to control the amplitude of the signal transmitted to the speaker, there being a manually controllable part on the housing connected with said adjustable means which includes a potentiometer coupled to the input of an output amplifier defined by said amplifier means, said part comprising a knob projecting from one side of the housing, said transducer including microphone protecting ring structure projecting from the opposite side of the housing opposite said knob,
   (g) said filter means comprising an adjustable low-pass filter means, there being a manually controllable element on the housing and connected with said adjustable low-pass filter means to adjust same, said element being movable between two positions, said low-pass filter means including first and second low-pass filters and switch means to connect one or both of said filters in series,
   (h) said enclosure having a tubular nipple defining only a single acoustic wave outlet port connected to a single flexible tubing of the stethoscope, said single tubing branching to become two tubings at a location spaced from the enclosure, the speaker acoustically facing toward said single outlet port,
   (i) said single outlet port being in lengthwise alignment with said single flexible tubing, and said flexible electrical connection means approaching said housing in alignment with said outlet port and said single flexible tubing, whereby the enclosure effectively becomes an extension of said single tubing and of said flexible electrical connection means, the tubing end removably telescopically fitting the nipple, (j) the housing including a one-hand graspable section with said knob and said manually controllable element located proximate one another yet projecting in different directions so as to be manipulable by the fingers of the user's hand, said first output terminal located at an end of said hand graspable section remote from said microphone.

2. The combination of claim 1 wherein said cord includes a plug, said first output terminal defining a first electrical socket, said circuitry having a second output terminal defining a second electrical socket, said sockets being carried by the housing and being alike so that each of them fits the plug, either socket adapted to receive a second plug connected with a recording and/or an associated display apparatus.

3. The combination of claim 2 including said second plug in the other socket, and said recording and/or associated display apparatus connected with the second plug.

* * * * *